US00PP21314P2

(12) United States Plant Patent
Kordes

(10) Patent No.: US PP21,314 P2
(45) Date of Patent: Sep. 28, 2010

(54) SHRUB ROSE PLANT NAMED 'KORPRIGGOS'

(50) Latin Name: *Rosa hybrida*
Varietal Denomination: KORpriggos

(75) Inventor: Tim-Hermann Kordes, Offenseth-Sparrieshoop (DE)

(73) Assignee: W. Kordee' Söhne Rosenschulen GmbH & Co KG, Offenseth-Sparrieshoop (DE)

( * ) Notice: Subject to any disclaimer, the term of this patent is extended or adjusted under 35 U.S.C. 154(b) by 137 days.

(21) Appl. No.: 11/893,516

(22) Filed: Aug. 15, 2007

(51) Int. Cl.
*A01H 5/00* (2006.01)

(52) U.S. Cl. ..... Plt./103

(58) Field of Classification Search ..... Plt./102, Plt./103
See application file for complete search history.

(56) References Cited

U.S. PATENT DOCUMENTS

PP10,639 P * 10/1998 Olesen et al. ..... Plt./102
2009/0038035 P1 * 2/2009 Kordes ..... Plt./107

OTHER PUBLICATIONS

UPOV ROM GTITM Computer Database GTI Jouve Retrieval Software 2008/04 Citation for 'KORpriggos'.*
QZ (CPVO) Application # 2006/1198 Aug. 15, 2006, W. Kordes' Söhne Rosenschulen GmbH & Co KG.

* cited by examiner

*Primary Examiner*—Wendy C. Haas

(57) ABSTRACT

A new and distinct variety of rose with long lasting, novel cream white flowers, with pale peach coloration in the center of the bloom, and attractive foliage with excellent disease resistance. It exhibits uniform, upright to bushy growth with abundant flowers. The new variety propagates well from cuttings and by grafting. This new and distinct variety has shown to be uniform and stable in the resulting generations from asexual propagation.

1 Drawing Sheet

Latin name of genus and species: The botanical classification of the new rose plant is *Rosa hybrida.*

Variety denomination: The denomination of the new variety is 'KORpriggos'.

CROSS REFERENCES AND FEDERAL R&D STATEMENT

There are no cross referenced or related applications. This variety was developed without the aid of any research grant.

BACKGROUND OF THE INVENTION

The new variety of rose plant of the present invention originated from a controlled crossing in a breeding program of two distinct parents during the summer of 1997. The crossing was between an un-named seedling and an un-named seedling.

The resulting seeds were planted during the following winter. The resulting seedlings were evaluated and exhibited distinctive physical and biological characteristics. The new rose plant was selected as a single plant from the seedling beds due to its superior characteristics and asexually propagated for further evaluation. This new and distinctive rose variety is named 'KORpriggos'.

SUMMARY OF THE INVENTION

The new rose plant may be distinguished from its seed parent, an un-named seedling by the following combination of characteristics:

1. 'KORpriggos' has cream white, very double flowers, while the seedling' un-named seedling has semi-double, pink flowers; and
2. 'KORpriggos' has an upright to bushy habit while the seedling' un-named seedling has an upright habit.

The new rose plant may be distinguished from its pollen parent, an seedling' un-named seedling by the following combination of characteristics:

1. 'KORpriggos' has cream white, very double flowers, while the seedling' un-named seedling has semi-double, pink flowers; and
2. Flowers of 'KORpriggos' have a light to moderate floral scent, while the seedling' un-named seedling lacks fragrance.

The objective of the hybridization was to create a new and distinct rose plant with unique qualities, such as:

1. Compact and uniform growth and flowering; when grown as a plant from cuttings;
2. Abundant attractive, recurrent flowers;
3. Attractive and abundant foliage; and
3. Resistance to diseases encountered in landscapes and gardens.

This combination of qualities is not present in prior rose cultivars known to the inventor. These objectives have been substantially achieved and in that distinguish 'KORpriggos' from all other varieties of which we are aware.

As part of a rose development program, Tim-Hermann Kordes germinated seeds from the aforementioned hybridization and conducted evaluations and observations on the resulting seedlings in a controlled environment in Offenseth-Sparrieshoop, Germany. The resulting seedlings exhibited distinctive physical and biological characteristics. The new rose plant 'KORpriggos' was selected in May, 1998 from the seedling beds to be asexually propagated for further evaluation. The first asexual propagation of 'KORpriggos' was done by budding to seedling understocks in July, 1998 at the inventor's nursery in Offenseth-Sparrieshoop, Germany.

This initial and other subsequent propagations conducted in controlled environments demonstrate that 'KORpriggos' reproduces true to type in successive generations of asexual reproduction.

BRIEF DESCRIPTION OF THE DRAWING

The accompanying color illustration shows as true as is reasonably possible to obtain in color photographs of this type, the typical characteristics of the buds, flowers, leaves, and stems of 'KORpriggos'.

DETAILED BOTANICAL DESCRIPTION

The following is a description of 'KORpriggos', as observed growing in July, 2007 in a nursery in Jackson County, Oreg. on plants of 3 years of age. Color references are made using The Royal Horticultural Society (London, England) Colour Chart, 2001 except where common terms of color are used.

For a comparison, several physical characteristics of the rose variety 'KORgretaum', a patented rose variety from the same inventor described and illustrated in U.S. Plant Pat. No. 16,937 and issued on Aug. 1, 2006 are compared to 'KORpriggos' in Chart 1.

CHART 1

| Characteristic | 'KORpriggos' | 'KORgretaum' |
|---|---|---|
| Flower color, ¼ open | Upper surface: Orange-White Group 159D. Lower surface, marginal zone: White Group 155D. Transitions to a large marginal zone of Yellow Group 2D. | Upper surface: White Group 157D. Lower surface: White Group 157D |
| Petal count. | Flower is double to very double, with 80 petals on average; | Flower is very double, with 75-80 petals, on average. |

Parents:

*Seed parent.*—An un-named seedling.

*Pollen parent.*—An un-named seedling.

Classification:

*Botanical classification.*—*Rosa hybrida*, 'KORpriggos'.

*Commercial classification.*—Shrub rose.

FLOWER AND FLOWER BUD

Blooming habit: Recurrent.

Flower bud:

*Size.*—Upon opening, 35 mm in length from base of receptacle to end of bud and 16-18 mm in diameter.

*Bud form.*—Short, with a broad base.

*Bud color.*—As sepals first unfold, bud color is a blend of colors. The marginal zone of the outer surface of the petal is Orange-White Group 159D. The color transitions to Orange-White Group 159B in the middle zone, and Yellow Group 2D in the basal zone of the outer surface of the petal. When ¼ open, the upper surface of petals is Orange-White Group 159D. The lower surface is White Group 155D in the marginal zone transitioning to Yellow Group 2D in the large basal zone.

*Sepals.*—Size: Average 22 mm long×7-8 mm wide. Shape: Generally triangular, with the apex narrowing to a point. Very weak foliaceous appendages on three of the five sepals. Base is flat at union with receptacle. Quantity: Five. Surface texture: Inner side: Limited numbers of white, short hairs. Outer surface: A few white hairs and stipitate glands present n the center of the sepal. Color: Upper surface Yellow-Green Group 146D. Lower surface: Yellow-Green Group 144B. Center of basal area: Yellow-Green Group 144C and 144D.

Receptacle:

*Surface.*—Smooth.

*Color.*—Yellow-Green Group 144B.

*Shape.*—Elongated funnel.

*Size.*—10 mm (h)×7-8 mm (w).

Peduncle:

*Surface.*—With numerous stipitate glands over entire length.

*Length.*—20-25 mm average length.

*Diameter.*—2.0 mm average diameter.

*Color.*—Yellow-Green Group 144B. Limited intonations on juvenile peduncles of Greyed-Red Group 179A.

*Strength.*—Variable. Most flowers nodding.

*Borne.*—Multiple flower buds per stem, most commonly 3-4 flower buds. Ranging from 2-5 buds per stem.

Flower bloom:

*Fragrance.*—Light to moderate.

*Duration.*—On the plant 3-5 days. Senesced petals drop away cleanly.

*Size.*—Medium flowered garden rose. Average flower diameter is 80-90 mm when open.

*Form.*—Shape of flower when viewed from the side: Upon opening, upper part: Flattened convex. Upon opening, lower part: Convex. Open flower, upper part: Flattened convex. Open flower, lower part: Flat.

Color:

*Upon opening, petals.*—Outermost petals: Outer Side: Marginal zone of Orange-White Group 159D. Middle zone is Yellow-White Group 158D. Basal zone is Yellow Group 2D. Inner Side: Marginal zone of Orange-White Group 159C. Middle zone is Yellow-White Group 158C. Basal zone is Yellow Group 2D. Innermost petals: Outer Side: Marginal zone of Orange-White Group 159D. Middle zone is Yellow-White Group 158D. Basal zone is Yellow Group 2D. Inner Side: Marginal zone of Orange-White Group 159A. Middle zone is Orange-White Group 159B. Basal zone is Yellow Group 2D.

*Upon opening, basal petal spots.*—Basal petal spot, outermost petals: Outer Side: Yellow Group 1D. Inner Side: Yellow Group 1C. Basal petal spot, innermost petals: Outer Side: Yellow Group 1C. Inner Side: Yellow Group 1B.

*After opening, petals.*—Outermost petals: Outer Side: White Group N155D. Inner Side: White Group N155C. Innermost petals: Outer Side: Marginal zone: Yellow-Orange Group 20C. Middle zone: Yellow Group 11C. Basal zone: Yellow Group 2D. Inner Side: Orange-White Group 158B.

*After opening, basal petal spots.*—Basal petal spot, outermost petals: Outer Side: Yellow Group 1D. Inner Side: Yellow Group 1D. Basal petal spot, innermost petals: Outer Side: Yellow Group 1D. Inner Side: Yellow Group 1D.

General tonality: On open flower Orange-White Group 155D. No change in the general tonality at the end of the 3rd day. Afterwards, general tonality is White Group N155C. Senescing to White Group N155B.

Petals:

*Petal count.*—Very double. Approximately 80 petals under normal conditions.

*Petal reflex.*—Petals reflex slightly.

*Petal edge.*—Entire.

*Petal shape.*—Variable. Apex shape from round to acute. Shape of base is deltoid to wedge-shaped.

*Petal Size.*—45 mm (l)×30 mm (w).

*Thickness.*—Average.

*Petal arrangement.*—Generally in a regular pattern with overlapping edges.

*Petaloids.*—Present. Average of 10 per flower. Petaloids are 25-30 mm long and 12-15 mm wide. Color of inner and outer side of petaloids: Marginal zone of Orange-White Group 159A. Middle zone is Orange-White Group 159B. Basal zone is Yellow Group 2D. Outer side: Surface texture is smooth. Shape is variable, generally round at apex and deltoid at base. Many petaloids with narrow and long basal area.

Reproductive organs:

*Pistils.*—Approximately 50-60 present. Stigmas: Location: Slightly superior in position to anthers. Color: Greyed-Yellow Group 160C. Styles: Length: 7-8 mm long. Color: Greyed-Yellow Group 160C.

*Stamens.*—Approximately 110-120 on average and regularly arranged. Anthers: Size: 2 mm long. Color: Yellow Group 8C. Pollen: None observed. Filaments: Color: Yellow Group 5C. Length: 6 mm.

*Seed/Hip formation.*—Forms hips readily. Color: Green Group 138A. 20 mm high×18 mm wide.

THE PLANT

*Plant growth.*—Vigorous. Upright to bushy habit. When grown as a budded nursery plant the average plant height is 100-120 cm and the average plant width is 80-100 cm.

*Stems.*—Stem color: Young wood: Green Group 138A. Intonations on juvenile stems of Greyed-Red Group 180C. Older wood: Green Group 138A. Stem surface: Young wood: Smooth. Older wood: Smooth.

*Prickles.*—Present. Incidence: 8-10 per 10 cm of stem. Size: Average length: 6 mm. Some thorns to 10 mm. Color: Immature prickles: Initially, Yellow-Green Group 145C at tips and Greyed-Red Group 180C at the base. Transitions to Yellow-Green Group 144C with diminishing intonations of Greyed-Red Group 180D. Mature prickles: Yellow-Green Group 144D. Senescing to Greyed-Orange Group 165B and 165B. Shape: Linear to deeply concave.

*Leaves and leaflets.*—Normally 7 leaflets on normal leaves in middle of the stem. Leaf size: Average of 110 mm (l)×80 mm (w). Ranging in size to 120 mm (l)×90 mm (w). Quantity: Abundant. Texture: Leathery. Upper side of leaflet: Glossy and smooth. Under side of leaflet: Matte and smooth. Color, mature foliage: Upper Leaf Surface: Green Group 137A. Lower Leaf Surface: Green Group 138A. Color, juvenile foliage: Upper Leaf Surface: Yellow-Green Group 146A. Lower Leaf Surface: Green Group 138B. Anthocyanin intonation: Present. Greyed-Red Group 180C. Location: Intonations present on juvenile leaves, peduncles, thorns, and stems.

*Stipules.*—Size: Average 14 mm (l)×5 mm (w). Ranging to 12-18 mm (l)×4-7 mm (w). Between tips of stipules, generally 12 mm. Stipule color: Green Group 138A. Presence of stipitate glands: Present on margins. Margins: Serrated.

*Petiole.*—Length: 15 mm. Diameter: 1.5-1.75 mm. Petiole color: Green Group 137A. Anthocyanin present on juvenile tissue. Greyed-Purple Group 180C. Underneath: Smooth. Prickles not observed. Stipitate glands: Limited numbers of stipitate glands on margins.

*Petiole rachis.*—Length: 15 mm. Diameter: 1.5-1.75 mm. Color: Green Group 137A. Anthocyanin present on juvenile tissue. Greyed-Purple Group 180C. Underneath: Smooth. Prickles: A few small prickles underneath. Stipitate glands: Limited numbers of stipitate glands on margins.

*Leaflets.*—Size: Average size of the terminal leaflet is 50-60 mm(l)×28-30 mm(w). Color: Upper side: Green Group 137A. Lower side: 138A. Leaflet shape: Base: Ovate. Apex: Ovate to acute. Margins: Serrated. Texture: Leathery.

Hips/seed formation: Forms hips readily. Large. 20 mm (h)×16 mm (l). Color: Green Group 138A.

Winter hardiness: To date, the variety has been grown successfully in Zone 5.

Disease resistance: Excellent resistance to Powdery mildew (*Sphaerotheca pannosa*), rust (*P. disciflorum*), blackspot (*Diplocarpon rosae*), and Botrytis (*Botrytis cinerea*), diseases under normal growing conditions.

I claim:

1. A new and distinct variety of rose plant as herein illustrated and described.

* * * * *

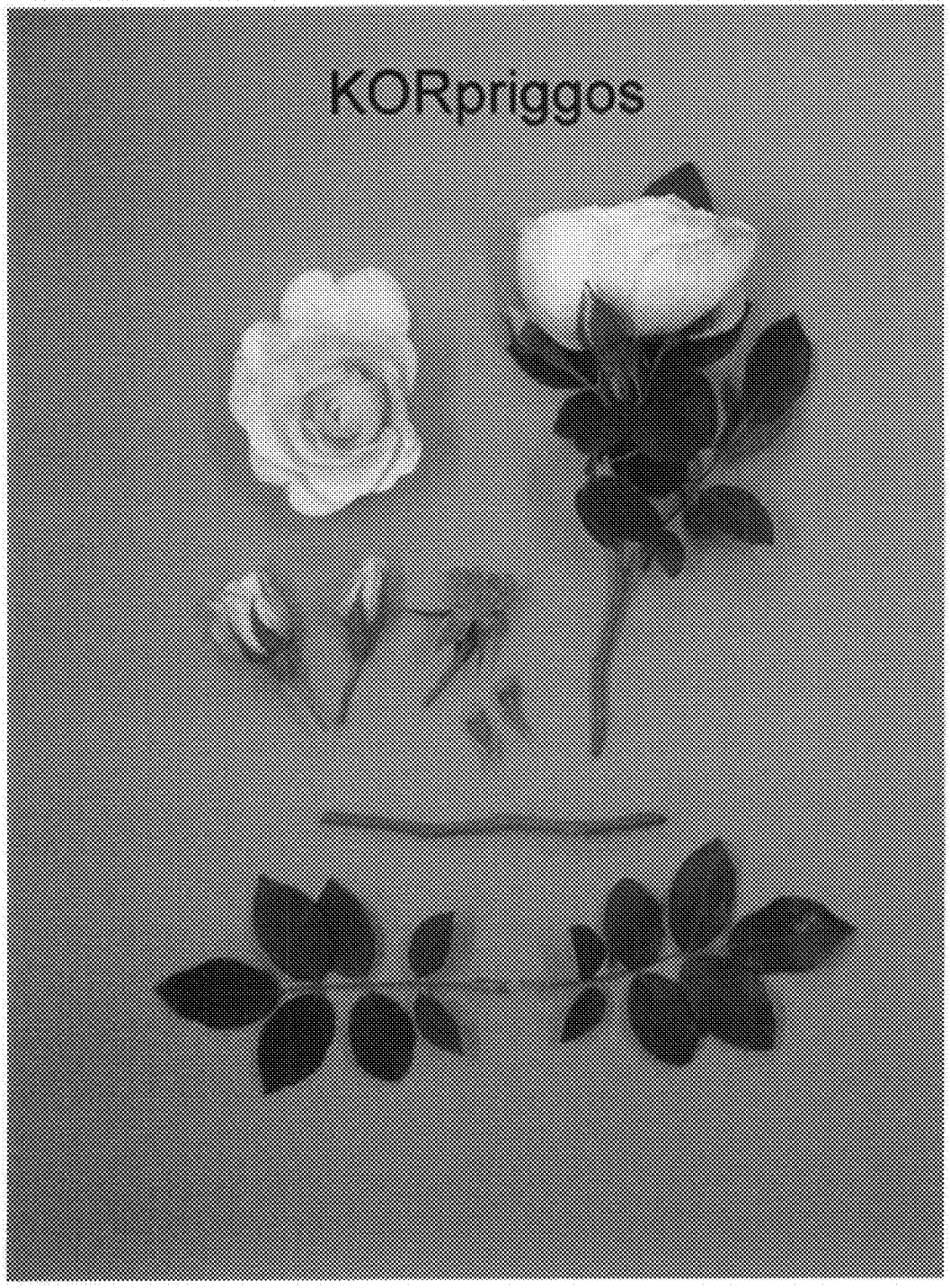
KORpriggos